United States Patent [19]

Heiser et al.

[11] Patent Number: 5,562,444
[45] Date of Patent: Oct. 8, 1996

[54] BRACKET

[76] Inventors: Wolfgang Heiser, Herzog-Sigmund-Ufer 17, A-6020, Innsbruck, Austria; Claus Schendell, Gutenbergstrasse 9, 82205, Gilching, Germany

[21] Appl. No.: 428,886

[22] Filed: Apr. 25, 1995

[51] Int. Cl.[6] .................................... A61C 7/00
[52] U.S. Cl. ............................................. 433/11
[58] Field of Search ........................ 433/8, 10, 11, 433/13

[56] References Cited

U.S. PATENT DOCUMENTS

| | | | |
|---|---|---|---|
| 3,871,096 | 3/1975 | Wallshein | 433/11 |
| 4,023,274 | 5/1977 | Wallshein | 433/11 |
| 4,144,642 | 3/1979 | Wallshein | 433/11 |
| 4,248,588 | 2/1981 | Hanson | 433/11 |
| 4,492,573 | 1/1985 | Hanson | 433/11 |
| 4,669,980 | 6/1987 | Degnan | 433/8 |
| 4,698,017 | 10/1987 | Hanson | 433/13 |

FOREIGN PATENT DOCUMENTS 4180750  6/1992  Japan ............................ 433/11

*Primary Examiner*—Cary E. O'Connor
*Attorney, Agent, or Firm*—Brooks Haidt Haffner & Delahunty

[57] ABSTRACT

A bracket having a movable closing spring fixedly but releasably attached thereto, wherein the closing spring is movable between two positions. The closing spring is retained in the opened and closed position due to the inherent spring force and can be put on and off the base member of the bracket.

20 Claims, 5 Drawing Sheets

FIG.1
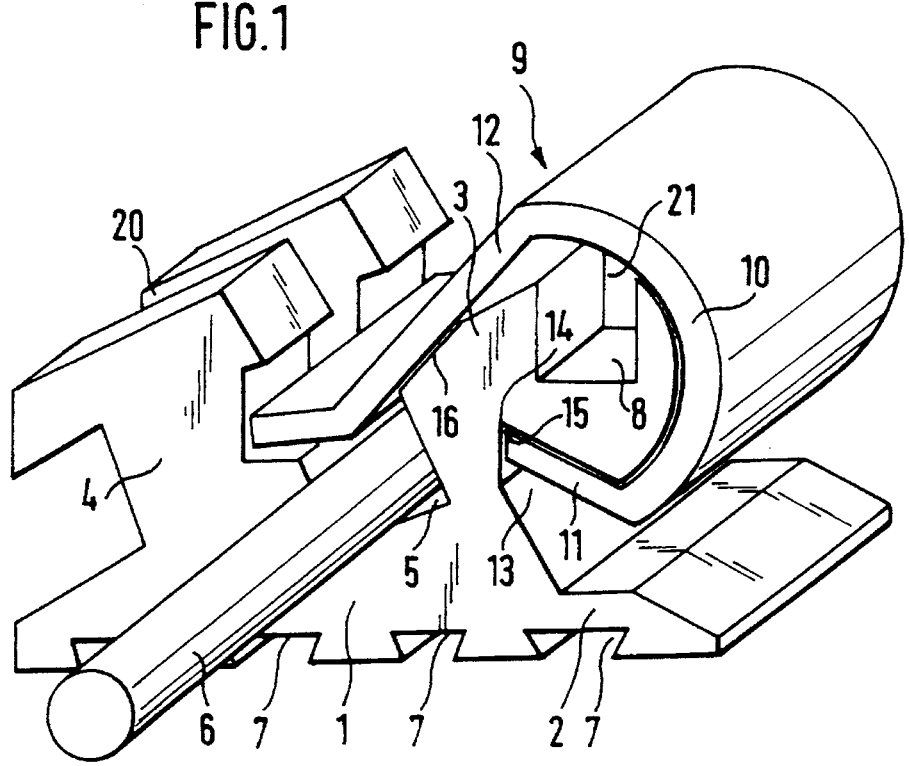
FIG.7       PRIOR ART
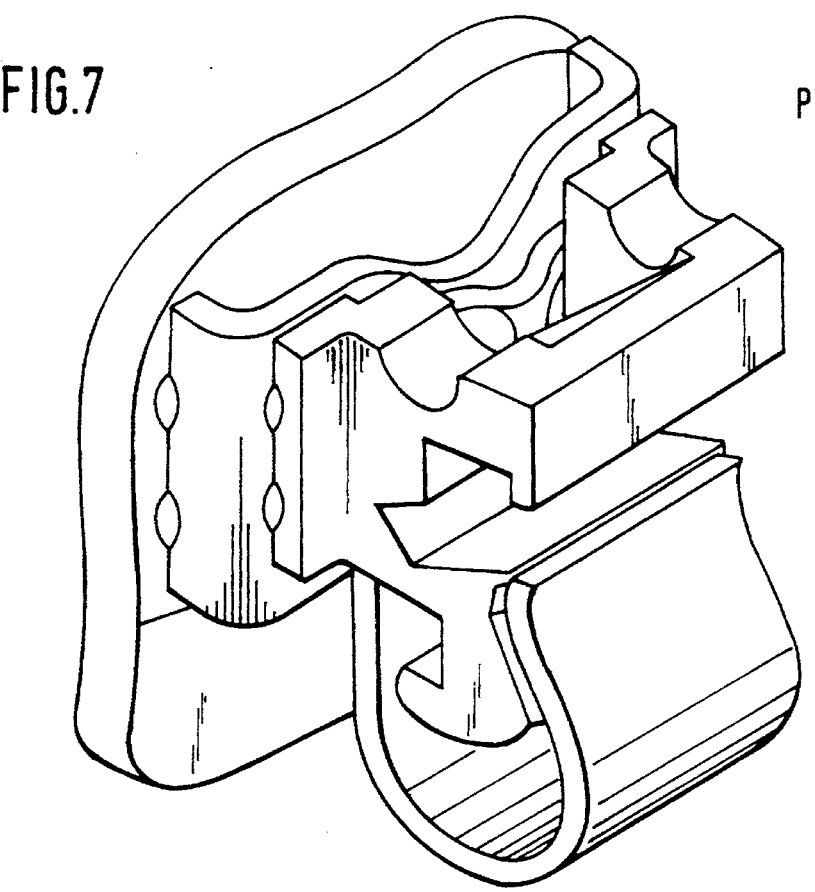

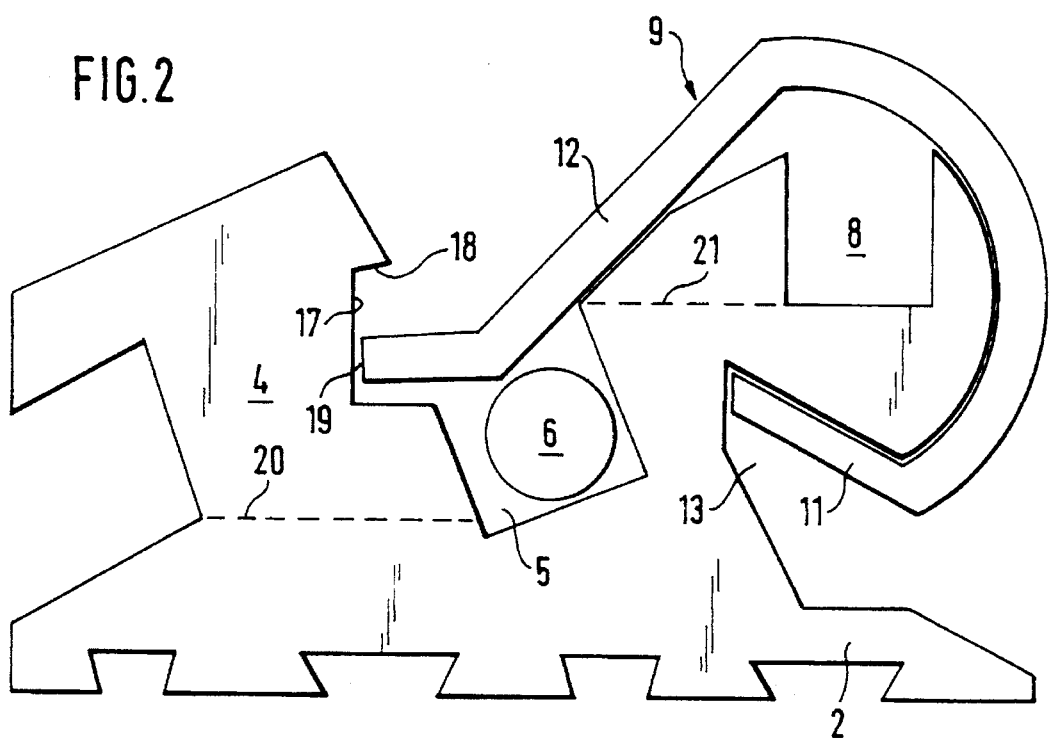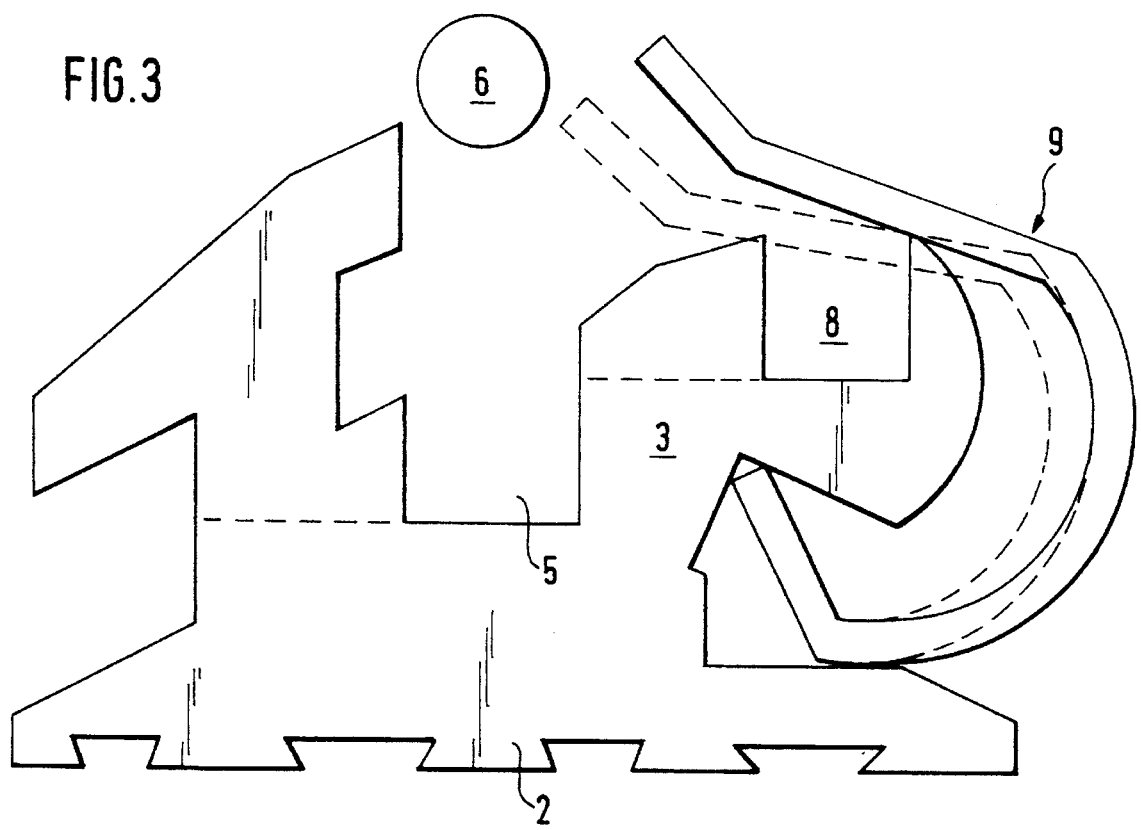

5,562,444

BRACKET

The present invention refers to a bracket for orthodontic treatments, comprising a base member having a bottom plate to be adhered to a tooth, and first and second holding arms projecting from the bottom plate and defining a slot between one another for receiving a wire, and of a spring retained by the base member and comprising an essentially U-shaped arc and essentially straight legs joining to said arc, wherein the U-shaped arc encloses the first holding arm, said spring being movable at the base member between two equilibrium positions, wherein in one position of said spring the slot is opened and in the other position the slot is covered by the spring.

Such a bracket is offered by Strite Industries Ltd., Cambridge, Ontario, Canada under the name Speed System and is shown in FIG. 8 of the attached drawings.

Brackets serve for eliminating false (defective) positions of the human teeth. They are adhered to the front side of the teeth at a predetermined position, and a wire (arch wire) is inserted into the slots formed at the brackets, said wire having a more or less wavy course at the beginning of the treatment corresponding to the false position of the teeth longitudinally to the row of teeth and thus causes forces at the brackets due to the elasticity of the wire which are transferred to the teeth, and gradually leads to the result that the teeth align in the manner desired by the orthodontist. During such an orthodontic treatment it is necessary to change the arch wire dependent on the evolution of the position of the teeth. Whereas relatively thin wires are used at the beginning of the treatment, these wires have to be exchanged by thicker and more rigid and even wires having a square cross section for minimizing tolerance at the brackets to thereby reach the desired final result. A disadvantage of the brackets to be alloyed is that an arch wire having a square cross section and which does not completely fill the slot in the bracket, has an undesired tolerance therein.

The brackets that are used most often are one-piece devices, consisting of a bottom plate and holding arms formed integrally therewith, between which the arch wire is inserted where it is fixed by means of a thin wire, a so-called ligature, which is wound around the free ends of the arms above the arch wire disposed in the slot, and is cabled with its ends. The cabled ends of the ligatures have to be carefully hidden at the brackets so that the patient is not disturbed more than unavoidable. It is also known to form the ligatures of rubber bands, which, however, suffer from the disadvantage that they have to be exchanged in relatively short intervals.

The frequent change of the arch wires and the removal and subsequent replacement of the ligatures made of wire or rubber, which is necessary when changing the arch wires, takes a lot of time. To overcome these disadvantages, the bracket shown in FIG. 7 has been developed. Therein, the slot for receiving the arch wire can be closed by means of a U-shaped leaf spring, which can be moved from the position shown in FIG. 7 so that its outer, shorter leg is disposed over the slot. The longer leg of this spring is located in a passage in the bottom plate of the bracket extending underneath the slot. That leg is hardly accessible when intending to open the bracket for changing the arch wire. Moreover, this passage makes the bottom plate unnecessarily high, which is uncomfortable for the patient. A further disadvantage is that the passage might be obstructed by adhesive which possibly penetrates into said passage when attaching said bracket to a tooth, and thereby makes the spring immovable. The longer leg of the spring is moreover provided with projections at its end which should prevent the spring from sliding out of the passage. Thus, the spring is not exchangeable at the bracket. If the spring is damaged, the entire bracket has to be replaced, i.e. it has to be removed from the tooth. Moreover, the bracket is relatively expensive.

It is an object of the present invention to provide a bracket of the aforementioned kind, which enables a quick and easy exchange of the arch wire, which can be easily opened, in which the spring is exchangeable but is reliably secured to the bracket, and which can be more easily manufactured.

This object is solved according to the invention by a bracket for orthodontic treatments, consisting of a base member having a bottom plate to be adhered to a tooth and first and second holding arms projecting from the bottom plate, which define a slot between one another for receiving a wire, and of a spring retained by the base member and comprising an essentially U-shaped arc and two essentially straight legs connected thereto, wherein the U-shaped arc encloses the first holding arm, and said spring being movable at the base member between two equilibrium positions, wherein in its one position the slot is opened and in the other position the slot is covered by a first one of the legs of said spring, wherein the second one of said legs of the spring is immovably retained by a free end thereof at the base member in a defined abutment position by the tension of the spring, and the first leg can be brought to the second position by resiliently, partially bending open the arc of the spring, in which position it is retained by elastic clamping at the first holding arms of the base member.

The spring suitably consists of a leaf spring, it can, however, also be a wire spring in which the free ends of the first straight legs are connected to one another by a wire web, extending parallelly to the slot of the base member.

In a first embodiment of the invention having a leaf spring, the first and second legs have a different length and extend at an angle of approximately 90° to one another, wherein the shorter leg is disposed in a groove, which is provided at a lower side of the first arm pointing against the bottom plate, and which has an end edge which is supported in a bottom of the groove, wherein the longer leg together with the end edge of the shorter leg of the first arm clamps in all positions of the leaf spring and the leaf spring is pivotable between the two positions, wherein the slot can be closed by the longer slot of the leaf spring.

Preferably, the first arm of the bracket has a surface, at which the longer leg off the leaf spring abuts in the position closing the slot, so that it can only be moved out of the closing position against its inherent spring force.

The groove is preferably limited by a surface at one side at which the short leg of the spring abuts when the slot is opened. This surface thus limits the pivot path of the spring and prevents a removal of the same from the base member. Furthermore, it is of advantage if the short leg of the spring has a length which is approximately as great as the distance between the bottom of the groove and the upper surface of the bottom plate. This also ensures a sufficient opening of the slot and a protection against the loss of the spring.

As an advantage, the second arm has a nose projecting against the slot. In the closing position of the leaf spring the end edge of the longer leg of the same is disposed under said nose. The leaf spring is thereby secured in its closing position.

A further advantageous alternative provides a slot in the second arm, which extends laterally to the direction of the slot determined for receiving the arch wire. Thereby it is very easy to grip under the end edge of the long spring leg by means of a tool, to pivot the spring leg from the closed position to the open position. The tool can be guided in this laterally extending slot under the leaf spring.

Instead of the aforementioned slot, a hole can also be provided in the first straight leg of the leaf spring, in which a hook-like tool can be inserted to pivot the spring from the closed position to the open position.

A further alternative provides that a slot is formed in the second parallel arm, said slot extending parallelly to the slot for the arch wire. The slot in the second arm is adapted to receive a second arch wire if complicated treatments require this. This slot in the second arm is covered by the same leaf spring which covers the slot disposed between the two arms. A further, transversely extending slot can be provided in the second arm to more easily remove the arch wire from the slot formed in the second arm, said transverse slot extending up to the bottom of the arch wire receiving slot. In this way, a tool can grip under the arch wire disposed in the slot and the arch wire can be lifted out of the slot.

In a second embodiment with a leaf spring, the first and second arms of the base member are laterally provided with a recess at the side facing the bottom plate, the second straight leg of the leaf spring has a slot in its center and the leg sections located at both sides of the slot are disposed within the recesses, which have a greater height than the thickness of the lead spring material, and the free ends of said leg portions are folded and abut at a section of the second arm disposed outside the recess.

In all embodiments, the base member is preferably a cast member, e.g. made of stainless steel, or it is cut from a solid blank. The spring, no matter whether it is a wire spring or a leaf spring, preferably consists of stainless steel. It can be slipped on the base member and holds on to the base member by itself. It can be removed therefrom by means of tools, if it is necessary to replace it.

A special advantage of the invention is that upon suitable dimensioning of the slot depth, the arch wire possibly having a square cross section, disposed under the spring end, is pressed to the bottom of the slot by the spring, so that even if the arch wire does not completely fill the slot, it is secured against tolerance. A torque acting on the root of the tooth or a so-called root torque in a pre-defined direction is caused by this pressure of the spring. Thus, a control of the desired root torque is achieved at an early state of the treatment.

DESCRIPTION OF THE DRAWINGS

FIG. 1 shows a bracket according to the invention having an inserted arch wire;

FIG. 2 is the lateral view of the bracket according to FIG. 1;

FIG. 3 is a modified embodiment of the bracket of FIG. 2 in opened condition of the leaf spring.

FIG. 7 shows a bracket according to the aforementioned prior art.

Figure 4:
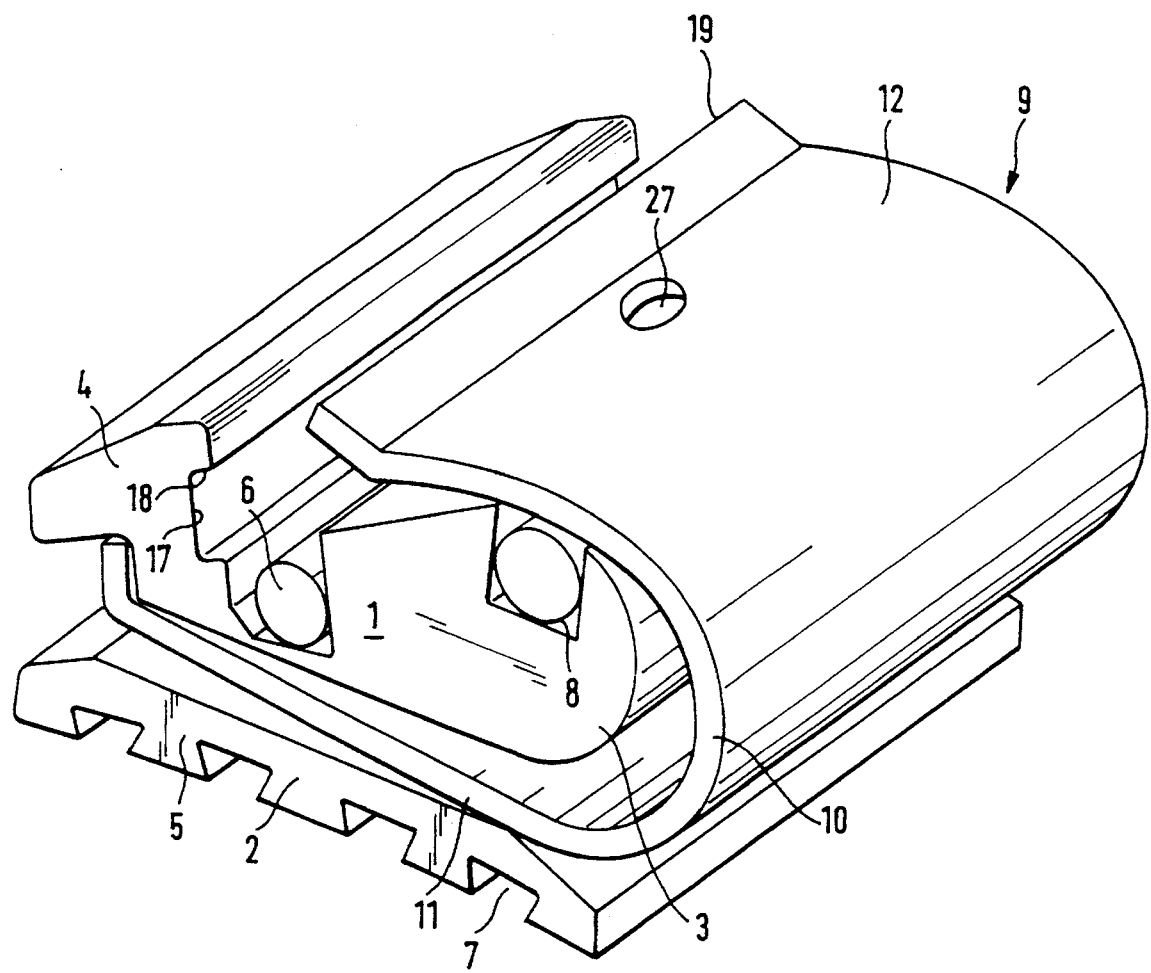
FIG. 4 is a perspective view of a second embodiment of the invention.
Figure 5:
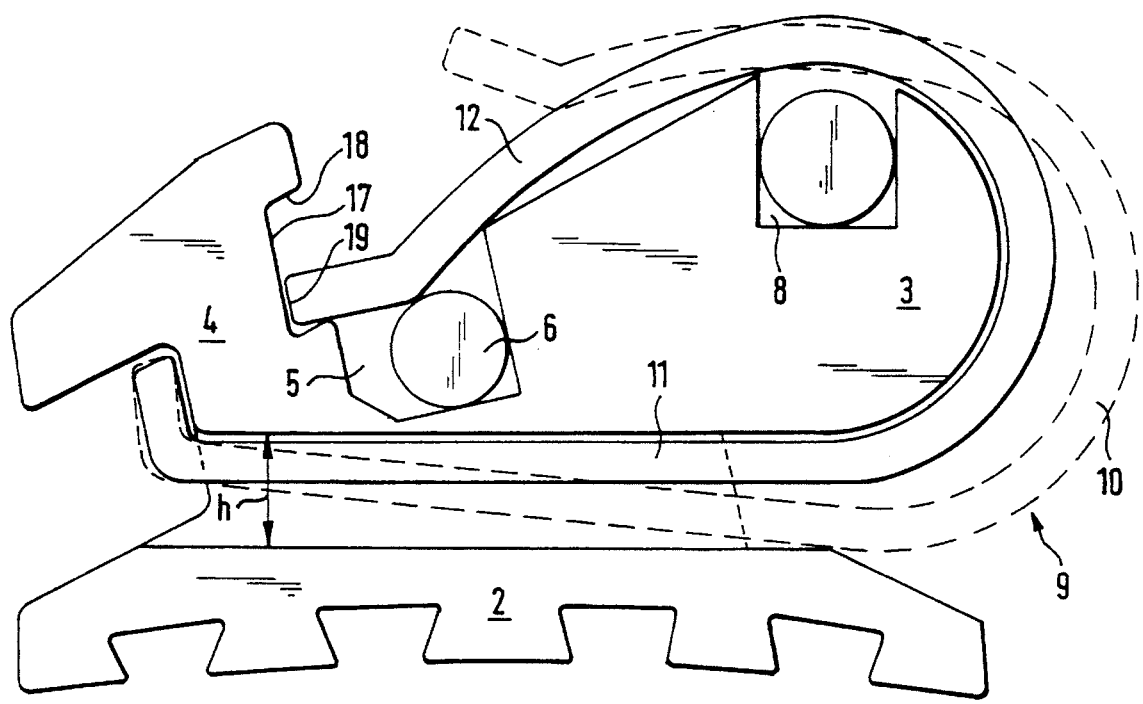
FIG. 5 is the lateral view of the embodiment according to FIG. 4.
Figure 6:
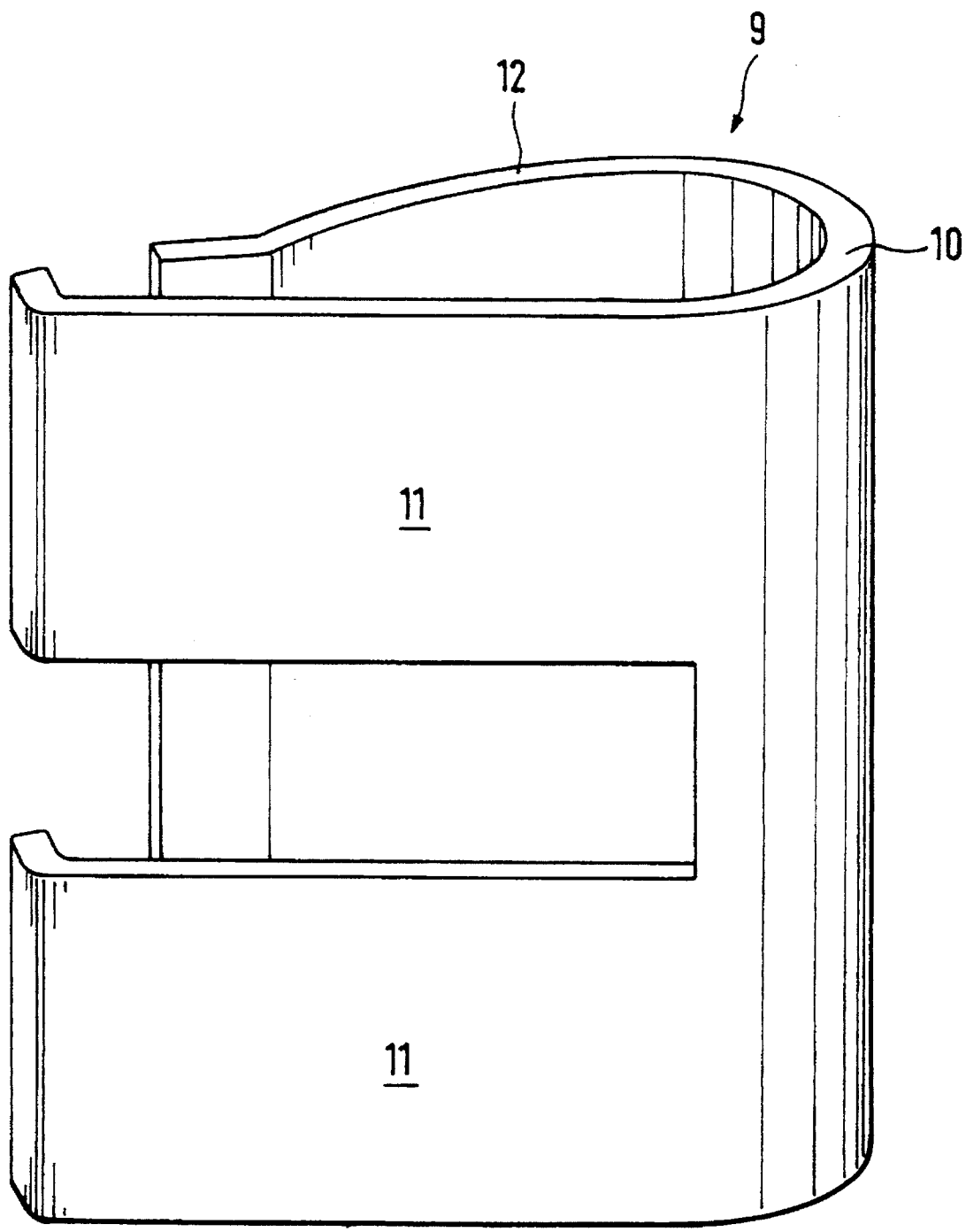
FIG. 6 shows the leaf spring for the embodiment according to FIGS. 4 and 5.

The bracket of FIG. 1 includes a base member 1 having a bottom plate 2, from which two arms 3 and 4 project. The arms 3 and 4 define a slot 5 inbetween in which an arch wire 6 is inserted in the shown example which extends through a plurality of brackets, preferably all brackets of a jaw. The bottom plate 2 comprises a plurality of swallowtail-shaped grooves 7 and is adapted to be adhered to a tooth, wherein the grooves 7 into which the adhesive penetrates, improve the adhesion of the bracket at the respective tooth.

The first arm 3 is provided with a slot extending parallelly to the slot 5, in which also an arch wire can be inserted.

The first arm 3 is surrounded by a leaf spring, in total designated by 9 and which has a U-shaped arc 10 of approximately 150° arc length, to which two essentially straight legs 11 and 12 of different length are connected. The legs 11 and 12 form an angle between one another of approximately 90°, and they enclose essentially the first arm 3 between one another and the U-shaped arc 10. The shorter leg 11 of the leaf spring 9 is disposed in a groove 13, which is formed at the lower side of the arm 3 pointing to the bottom plate 2. This groove is of generally wedge-shaped cross section and it has a bottom 14 at which an end edge 15 of the shorter spring leg 11 is supported. The leaf spring 9 has a bias, which results in that the first leg 3 is clamped between between the end edge 15 of the first spring leg 11 and the longer leg 12, which planarly rests on a planar surface 16 at the first arm 3. This clamping effect is existing in all positions of the leaf spring 9 as will be explained later.

The second arm 4 has a recess 17 on the side facing the slot 5, which forms a nose 18 at its upper end, at which the end edge 19 of the long spring leg 12 can snap in. The leaf spring 9 is thereby secured against unintended opening.

The second arm is provided with a transversely extending slot 20 approximately in the middle of the arm, which extends approximately to the bottom of the slot 5. This slot 20 is adapted to make the free edge 19 of the long spring leg accessible by a tool means of which the leaf spring 9 may be opened. Alternatively, it can be abstained from providing the slot 20 and instead a hole 27 shown in FIG. 4 can be provided in the long spring leg 12, into which a hook-like tool for opening the leaf spring may be inserted. This alternative, which will be explained by the aid of the second embodiment of the invention, is shown in FIG. 4 and can also be used in the bracket according to FIG. 1. A laterally extending slot 21 comparable to slot 20 can also be provided in the first arm 3, to be able to lift the wire (not shown in the drawings), located in the slot 8, out of the slot 8 by means of a tool.

FIG. 3 shows an embodiment of the invention, in which the slot 5 in contrast to the embodiment according to FIG. 2, does not extend inclined with respect to the bottom plate 2 but perpendicularly to the bottom plate 2. Moreover, it is shown in FIG. 3 that the leaf spring 9 has to bend open against the intrinsic spring force when being opened, in order to slide over the contour of the first arm 3. The condition which would be taken by the spring in relieved state is shown in dotted lines, whereas the true condition in the open position is shown in full lines. Due to the elastic deformation of the spring 9, this spring is not only retained in its open position but it is also secured against a lateral sliding off of the base member 1.

For practical use, the base member is to be adhered to the tooth by means of a suitable adhesive. The leaf spring is then pivoted to the open position by the aid of a hook-like tool. After inserting and aligning the arch wire into slot 5 (and possibly another arch wire into slot 8), the leaf spring 9 is pivoted to the closed position, wherein the end edge 19 of its long leg latches under the nose 18. Moreover, the leaf spring 9 is retained in the clamping position due to its inherent spring force.

For opening the bracket, it is gripped under the end edge 19 of the leaf spring by means of a hook-like tool and the leaf spring is pivoted to the open position.

We claim:

1. A bracket for orthodontic treatments, comprising a base member having a bottom plate to be adhered to a tooth, and first and second holding arms projecting from the bottom plate and defining a slot between one another for receiving a wire, and a leaf spring retained by the base member and comprising an essentially U-shaped arc and two essentially straight legs joining to said arc, wherein the U-shaped arc encloses the first holding arm, said leaf spring being movable at the base member between two equilibrium positions, wherein in a first of said positions of said leaf spring the slot is opened and in the other position of said leaf spring the slot is covered by a first one of said legs of the leaf spring, wherein the second one of said legs of said leaf spring comprises a free end which is immovably retained at the base member by means of a tension of said leaf spring in a defined abutment position, and said leaf spring may be brought into the second one of said positions by resiliently, partially bending open the arc of the leaf spring, in which it is retained by resiliently clamping said first leg at the first arm of the base member, and wherein the legs of said leaf spring have different lengths and extend at an angle of approximately 90° to one another, a shorter one of said legs being disposed in a recess provided at a lower surface of the first arm pointing against the bottom plate, and having an end edge abutting at the bottom of the recess, a longer one of said legs together with said end edge of the shorter leg clamping the first arm in all positions of the leaf spring, the leaf spring being pivotal between the two equilibrium positions, wherein the slot can be closed by the longer leg of the leaf spring.

2. A bracket according to claim 1, wherein the first arm comprises a surface at which the longer leg of the leaf spring flatly abuts in the spring position closing the slot.

3. A bracket according to claim 1 or 2, wherein the recess is limited at one side by a surface, at which the shorter leg of the leaf spring abuts in the spring position opening the slot.

4. A bracket according to claim 3, wherein the shorter leg of the leaf spring has a length, which is approximately as great as a distance between the bottom of said recess and an upper surface of the bottom plate.

5. A bracket according to claim 4, wherein a slot is provided in the second arm, extending transversely to the slot adapted to receive the wire.

6. A bracket according to claim 3, wherein the second arm comprises a nose projecting against the slot, underneath which in the closing position of said leaf spring an end edge of the longer spring leg is disposed.

7. A bracket according to claim 3, wherein a slot is provided in the second arm, extending transversely to the slot adapted to receive the wire.

8. A bracket according to claims 1 or 2, wherein the shorter leg of the leaf spring has a length, which is approximately as great as a distance between the bottom of said recess and an upper surface of the bottom plate.

9. A bracket according to claim 8, wherein the second arm comprises a nose projecting against the slot, underneath which in the closing position of said leaf spring an end edge of the longer spring leg is disposed.

10. A bracket according to claim 9, wherein the slot provided in the second arm extends approximately to a level of the bottom of the slot adapted to receive the wire.

11. A bracket according to claim 8, wherein a slot is provided in the second arm, extending transversely to the slot adapted to receive the wire.

12. A bracket according to claim 11, wherein the slot provided in the second arm extends approximately to a level of the bottom of the slot adapted to receive the wire.

13. A bracket according to claim 11, wherein a second slot is provided in the first arm, extending transversely to the slot provided in the first arm and extending to the bottom thereof.

14. A bracket according to claims 2, wherein the second arm comprises a nose projecting against the slot, underneath which in the closing position of said leaf spring an end edge of the longer spring leg is disposed.

15. A bracket according to one of claims 1 or 2, wherein a slot is provided in the second arm, extending transversely to the slot adapted to receive the wire.

16. A bracket according to claim 15, wherein a second slot is provided in the first arm, extending transversely to the slot provided in the first arm and extending to the bottom thereof.

17. A bracket according to one of claims 1 or 2, wherein another slot is provided in the first arm, extending parallelly to the slot between said arms.

18. A bracket according to claim 1 or 2, wherein a hole is on the first leg of the leaf spring.

19. A bracket according to claim 1 or 2, wherein the first leg of the leaf spring comprises a short central slot at a free end thereof.

20. A bracket for orthodontic treatments, comprising a base member having a bottom plate to be adhered to a tooth, and first and second holding arms projecting from the bottom plate and defining a slot between one another for receiving a wire, and a leaf spring retained by the base member and comprising an essentially U-shaped arc and two essentially straight legs joining to said arc, wherein the U-shaped arc encloses the first holding arm, said leaf spring being movable at the base member between two equilibrium positions, wherein in a first of said positions of said leaf spring the slot is opened and in the other position of said leaf spring the slot is covered by a first one of said legs of the leaf spring, wherein the second one of said legs of said leaf spring comprises a free end which is immovably retained at the base member by means of a tension of said leaf spring in a defined abutment position, and said leaf spring may be brought into the second one of said positions by resiliently, partially bending open the arc of the leaf spring, in which it is retained by resiliently clamping said first leg at the first arm of the base member, and wherein the first and second arms of said base member are laterally provided each with a recess at a side facing the bottom plate, the second leg of the leaf spring comprising a slot in a center thereof and the leg portions being located at both sides of the slot being disposed in the recesses, said recesses each having a greater height (h) than a thickness of the leaf spring material, and that said leg sections have free ends which are bent and abut at a section of the second arm disposed outside said recesses.

* * * * *